US006703399B2

(12) United States Patent
Cao et al.

(10) Patent No.: US 6,703,399 B2
(45) Date of Patent: Mar. 9, 2004

(54) HALO-ALKYL ESTERS OF CAMPTOTHECINS AND METHODS OF TREATING CANCER USING THESE COMPOUNDS

(75) Inventors: Zhisong Cao, Friendswood, TX (US); Beppino C. Giovanella, Houston, TX (US)

(73) Assignee: The Stehlin Foundation for Cancer Research, Houston, TX (US)

( * ) Notice: Subject to any disclaimer, the term of this patent is extended or adjusted under 35 U.S.C. 154(b) by 3 days.

(21) Appl. No.: 10/139,817

(22) Filed: May 6, 2002

(65) Prior Publication Data

US 2003/0212087 A1 Nov. 13, 2003

(51) Int. Cl.[7] .................... A61K 31/435; C07D 491/22
(52) U.S. Cl. ........................ 514/283; 546/14; 546/48
(58) Field of Search .............. 546/48, 14; 514/283

(56) References Cited

U.S. PATENT DOCUMENTS

| | | | |
|---|---|---|---|
| 4,399,282 A | 8/1983 | Miyasaka et al. | 546/48 |
| RE32,518 E | 10/1987 | Miyasaka et al. | 546/48 |
| 5,552,154 A | 9/1996 | Giovanella et al. | 424/449 |
| 5,652,244 A | 7/1997 | Giovanella et al. | 514/283 |
| 5,731,316 A | 3/1998 | Cao et al. | 514/283 |
| 5,880,131 A | 3/1999 | Greenwald et al. | 514/279 |
| 5,889,017 A | 3/1999 | Giovanella et al. | 514/283 |
| 5,922,877 A | 7/1999 | Cao | 546/48 |
| 5,965,566 A | 10/1999 | Greenwald et al. | 514/279 |
| 5,968,943 A | 10/1999 | Cao et al. | 514/283 |
| 6,040,313 A | 3/2000 | Wall et al. | 514/283 |
| 6,080,751 A | 6/2000 | Stehlin et al. | 514/283 |
| 6,096,336 A | 8/2000 | Cao et al. | 424/449 |
| 6,120,793 A | 9/2000 | Cao et al. | 424/449 |
| 6,166,029 A | 12/2000 | Giovanella et al. | 514/283 |
| 6,218,399 B1 | 4/2001 | Cao et al. | 514/283 |
| 6,228,855 B1 | 5/2001 | Cao et al. | 514/224.2 |
| 6,342,506 B1 | 1/2002 | Giovanella et al. | 514/283 |
| 6,350,756 B1 | 2/2002 | Yang et al. | 514/283 |
| 6,407,118 B1 | 6/2002 | Cao et al. | 514/283 |
| 6,407,239 B1 | 6/2002 | Cao et al. | 546/48 |
| 2001/0031761 A1 | 10/2001 | Cao et al. | 514/283 |
| 2002/0049324 A1 | 4/2002 | Cao et al. | 546/48 |

FOREIGN PATENT DOCUMENTS

WO   WO 03/014069   2/2003

OTHER PUBLICATIONS

Article, "Plant Antitumor Agents," by Wall et al., Journal of Medicinal Chemistry, 1993, vol. 36, No. 18, p. 2689–2700.
Article, "Camptothecin–20–PEG Ester Transport Forms: the Effect of Spacer Groups on Antitumor Activity," by Greenwald et al., Bioorganic & Medicinal Chemistry 6, 1998, p. 551–562.
International Search Report, dated Sep. 1, 2003, for PCT/US03/12650.

*Primary Examiner*—Bernard Dentz
(74) *Attorney, Agent, or Firm*—Kilyk & Bowersox P.L.L.C.

(57) ABSTRACT

Halo-alkyl esters of camptothecin are described. Processes for making these compounds and for using them in cancer treatment, are also described.

56 Claims, No Drawings

HALO-ALKYL ESTERS OF CAMPTOTHECINS AND METHODS OF TREATING CANCER USING THESE COMPOUNDS

FIELD OF THE INVENTION

The present invention is directed to halo-alkyl esters of camptothecin and is also directed to compositions including derivatives of halo-alkyl esters of camptothecin in delivery systems, preferably derivatives having low toxicity and side effects. The present invention also relates to the use of these derivatives for cancer or tumor treatment in mammals. The disclosures of all documents referred to in this application are incorporated herein in their entirety by reference.

BACKGROUND OF THE INVENTION

Camptothecin, a cytotoxic alkaloid first isolated from the wood and bark of Camptotheca Acuminata (Nyssaceae) by Wall and his coworkers (*J. Am. Chem. Soc.* 88, 3888, 1966), was shown to have antitumor activity against the mouse leukemia L 1210 system. The structure of camptothecin, an alkaloid which has a commonly occurring indole alkaloid group (Heckendorf et al, *J Org. Chem.* 41, 2045, 1976), is shown below as Formula (X).

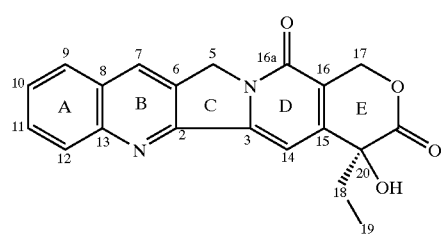

This compound ("CPT") has a pentacyclic ring system with only one asymmetrical center in ring E with a 20(S)-configuration. The pentacyclic ring system includes a pyrrolo [3, 4-b] quinoline moiety (rings A, B and C), a conjugated pyridone (ring D), and a six-membered lactone (ring E) with an α-hydroxyl group. Camptothecin was of great interest from the time of its initial isolation due to its noteworthy activity in the mouse leukemia L 1210 system. Earlier data for the antitumor activity of camptothecin were obtained by employing experimentally transplanted malignancies such as leukemia L 1210 in mice, or Walker 256 tumor in rats (*Chem. Rev.* 23, 385, 1973, *Cancer Treat. Rep.* 60, 1007, 1967). Subsequent clinical studies showed that this compound was not usable as an anticancer agent in vivo due to its high toxicity. Camptothecin itself is insoluble in water. Therefore, camptothecin was evaluated clinically as a water-soluble sodium carboxylate salt in the early times. This form of camptothecin produced severe toxicity and seemed devoid of anticancer activity (Gottlieb et al, *Cancer Chemother. Rep.* 54, 461, 1970, and 56, 103, 1972, Muggia et al, *Cancer Chemother. Rep.* 56, 515, 1972, Moertel et al, *Cancer Chemother. Rep.* 56, 95, 1972, and Schaeppi et al, *Cancer Chemother. Rep.* 5:25, 1974). These results caused the discontinuation of phase II trials. Continued evaluation of this agent showed that the sodium carboxylate salt is only 10% as potent as the native camptothecin with the closed lactone ring intact (Wall et al, *In International Symposium on Biochemistry And Physiology of The Alkaloids*, Mothes et al, eds, Academie—Verlag, Berlin, 77, 1969, Giovanella et al, *Cancer res.* 51, 3052, 1991). In addition, important parameters for antitumor activity in the camptothecin family have been established (Wall et al, *Ann. Rev., Pharmacol. Toxicol.* 17, 117, 1977). These results indicate that an intact lactone ring E and α-hydroxyl group are essential for antitumor activity.

In 1989, Giovanella et al. found that some of the non-water soluble derivatives of camptothecin have high antitumor activity against xenograft of human tumors (Giovanella et al., *Science*, 246, 1046, 1989). It has also been shown that administration of camptothecin with closed lactone ring is superior to injections of water-soluble carboxylate salt (Giovanella et al, *Cancer Res.*, 51, 3052, 1991). These findings further confirmed the importance of the intact lactone ring to biological activity.

Ring opening of 20(S)-camptothecin ("CPT") leads to much more potent anticancer activity in mice than in humans. In effect, CPT administered intramuscularly ("i.m."), subcutaneously ("s.c."), and intrastomach ("i.s.") has proved to be a very potent anticancer agent against human tumors in mice, i.e., when growing as xenotransplants in nude mice (Giovanella et al, Cancer Res. 51:3052, 1991). However, when tumors were treated with CPT in humans, a lower degree of anticancer activity in humans, than in mice, was exhibited (Stehlim et al., In Camptothecins: New Anticancer Agents, 1995, CRC Press, pp. 59–65).

The same phenomenon was observed with other CPT-derivatives. In mice, 9-nitrocamptothecin ("9NC") has proven to be 2–3 times more potent than CPT against human tumor xenografts causing the total eradication of all the human malignancies treated (Pantazis et al., Cancer Res. 53:1577, 1993; Pantazis et al., Int. J. Cancer 53:863, 1995).

Pharmacological studies demonstrated that the majority (57%) of the 9NC drug present in the plasma after i.s. administration is in the closed lactone form. Pharmacological studies on the plasma levels of 9NC after oral administration to Phase I clinical trial patients demonstrate that, on average, only ~3% of the drug present is in the closed lactone form.

In perfect agreement with such findings, the clinical responses in this group of patients, although higher than those obtained with CPT are still a far cry below the results obtained in mice (32/32 complete tumor regressions in mice versus 2/32 in humans). Clearly, there is a pressing need for a modification which will slow and delay the lactone ring opening upon its entrance into the blood circulation.

Ring opening is particularly problematic in that camptothecins exist in two distinct forms at physiological pH, i.e., 7 or above, as shown in the following equilibrium equation:

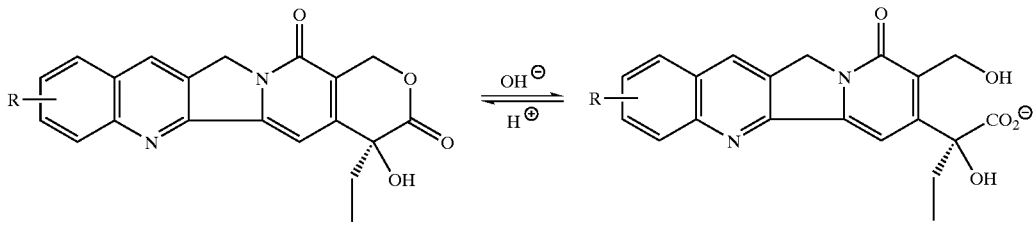

The hydrolysis reaction of the biological active lactone ring of camptothecins with water at higher pH gives the biologically inactive open form. Additionally, the hydrolysis problem with CPT and its analogs is exacerbated in human blood because the predominant blood serum albumin preferentially binds to the carboxylate form, which shifts the lactone/carboxylate equilibrium toward the inactive form (J. Biochem., 212, 285–287, 1993; Biochemistry, 33, 10325–10336, 1994; Biochemistry, 33, 12540–12545, 1994). Accordingly, preserving the lactone ring of the molecule for a sufficient time for the tumor cells to cycle through the S-phase is a major challenge and has been the focus of a considerable amount of research.

A number of attempts have been made to provide derivatives of camptothecin having greater biological activity and enhanced stability. Many of these compounds are the products of modifications on the A, B, and C rings of the molecule, but few of these modifications have enhanced the stability of the lactone ring under physiological conditions. Other approaches have been more successful. For instance, acylating of 20-OH group provides a useful tool for the protection of lactone ring E. Wall et al., U.S. Pat. No. 4,943,579, describes several acylated camptothecin compounds having water solubility, although the lactone may not remain intact under physiological conditions. U.S. Pat. No. 5,968,943 to Cao et al. discloses CPT-derivatives which are effective antitumor agents. Unfortunately, because mammalian physiological conditions break down all known CPT-derivatives, a need still exists for new CPT-derivatives and associated delivering systems for medical purposes.

In particular, there is a continuing need to modify 20(S)-camptothecin to enable the lactone ring to remain intact at normal physiological conditions, while retaining the structural elements, i.e. 20-hydroxyl and lactone ring E, for its antitumor activity. Accordingly, the present invention describes new CPT-derivatives which delay the opening of the lactone ring E, enhancing and prolonging the antitumor activity as compared to the mother analog, CPT.

SUMMARY OF THE INVENTION

Accordingly, it is an object of the present invention to provide halo-alkyl esters of camptothecins which remain intact longer in a mammalian body, particularly in a human body.

It is another object of the present invention to provide new CPT-derivatives which retain the lactone ring E and the 20-hydroxyl group intact, which are important for antitumor or anticancer activity.

It is still another object of the present invention to use these compounds in a liposomal delivery system for living mammals.

Additional objects and advantages of the present invention will be set forth in part in the description which follows, and in part will be apparent from the description, or may be learned by practice of the present invention. The objects and advantages of the present invention will be realized and attained by means of the elements and combinations particularly pointed out in the appended claims.

To achieve the objects and in accordance with the purpose of the present invention, as embodied and broadly described herein, the present invention relates to a compound of the formula:

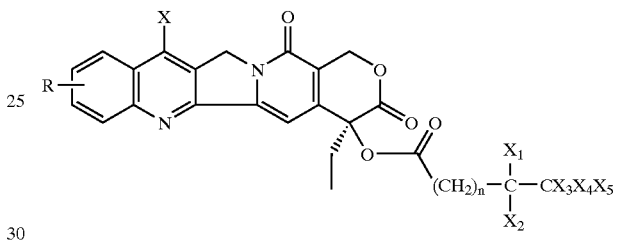

In this formula, the R group represents one or more substituents on one of the rings of the structure above. In particular, R can represent H, $NO_2$, $NH_2$, $N_3$, —OH, a halogen (e.g., F, Cl, Br, I), carboxyl (COOH), a $C_{1-16}$ alkyl group, a $C_{2-16}$ alkenyl group, a $C_{3-8}$ cycloalkyl group, a $C_{1-8}$ alkoxyl group, an aroxyl group, CN, $SO_3H$, a $C_{1-8}$ halogenated alkyl group, $(CH_2)_n NR_2^7$ (where $R^7$ can be H, or a $C_{1-8}$ alkyl group, n is an integer of from 1 to about 8), hydroxyl, SH, $SR^8$ (where $R^8$ can be a $C_{1-8}$ alkyl group, or an unsubstituted phenyl group, or a substituted phenyl group), a carbonyl group, (e.g., $COR^9$, where $R^9$ can be a $C_{1-8}$ alkyl group, or a phenyl group, or a substituted phenyl group), a $SiR_3^{10}$ (where $R^{10}$ can be a $C_{1-4}$ alkyl group). The R group can be respectively positioned at the 9, or 10, or 11, or 12 position of ring A. R can also be a disubstituted 10, 11-O—$(CH_2)_y$—O— group (where y can be an integer of from 1 to 3). R can also be $C_{2-12}$ alkenyl group(s), $CF_3$(s), $CCl_3$(s), $CH_2F$(s), $CH_2Cl$(s), $CHF_2$(s), $CHCl_2$(s), OH(s), $OR^{12}$(s) (where $R^{12}$ can be a $C_{1-8}$ alkyl group, or a $C_{2-8}$ alkenyl group, or an aromatic group), $NR_2^{13}$ (s) (where $R^{13}$ can be H, or $C_{1-4}$ alkyl group). X represents H, a $C_{1-8}$ alkyl group, a $C_{2-8}$ alkenyl group, a $C_{1-8}$ alkoxyl group, an aroxyl group, a $SiR_3^{11}$ group (where $R^{11}$ can be a $C_{1-4}$ alkyl group), or $CH_2NZY$ where Z and Y are, independently, H, $C_{1-4}$ alkyl, or a $C_{1-4}$ halogenated alkyl group. Preferably, R can be H, halogen, halogen containing group, alkyl group (e.g. $C_1-C_{15}$ alkyl group), —OH, alkoxy, $NH_2$, or $NO_2$, n=0–18; and $X_1$, $X_2$, $X_3$, $X_4$, and $X_5$, which can be the same or different, can be H, a substituted or unsubstituted alkyl group, or a halogen atom, a nitro group, cyano group, amino group, hydroxyl group, carbonyl group, or carboxyl group with the proviso that at least one of $X_1$ through $X_5$ is a halogen atom or a halogen containing group.

The present invention also relates to a method for treating cancer and/or malignant tumors in a mammal and comprises administering an effective amount of one or more of the above CPT-derivatives, which may include any delivery system or other therapeutic means.

Also, the present invention relates to methods of making the compounds of the present invention to provide halo-alkyl esters of camptothecins which remain intact longer in a mammalian body, particularly in a human body.

DETAILED DESCRIPTION OF THE INVENTION

In the most general sense, the present invention relates to halo-alkyl esters of camptothecins and their use for medicinal purposes. Camptothecins ("CPTs") have considerable anti-tumor and anti-cancer activity, but these compounds are susceptible to degradation under normal physiological conditions, and the metabolites produced often exhibit toxic properties. Therefore, the present invention provides CPT analogues which remain intact longer in a mammalian body, particularly in the human body, thus enhancing the anti-tumor and anti-cancer effects without producing undesirable side effects. In another embodiment, the present invention provides new CPT-derivatives which retain the lactone ring E and the 20-hydroxyl group intact, as prior research has shown that these structural features are important for anti-tumor or anticancer activity. The compounds of the present invention are bio-active and/or are a pro-drug that generates into a bio-active compound.

Metabolism studies of camptothecin in human plasma carried out in the laboratory showed that the only metabolite detected is the ring-opened sodium carboxylate salt which is toxic and inactive. The measurement of pharmacokinetics for CPT in human plasma indicates that the half-life time of the drug with lactone intact is 30 min. These results imply that the drug will lose 90% of its activity and produce many toxicities or side effects in a very short time after a patient takes it.

Comparative pharmacological studies in mice and humans have demonstrated that in mice the majority of the CPT present in the plasma after intrastomach administration is of the closed lactone form, approximately 54% of the area under the curve. In humans, on the contrary, only about 0.4% of the area under the curve after oral administration of CPT is in the form of closed lactone ring.

This difference between a mouse and a human is caused by the fact that although the blood pH of the mouse and human are the same, i.e., 7.4, the human albumin, which catalyzes the conversion of CPT into its sodium salt is ~100 times more efficient in this process than mouse albumin (Mi and Burke, Biochem. 33:12540, 1994).

In view of the different success rates in using CPT analogs as anticancer or antitumor agents in mice and humans, as discussed previously, it is clear that delaying the opening of the lactone ring under biological conditions is essential to enhance the beneficial properties of CPTs, as well as avoiding the negative side effects of metabolites. Therefore, to achieve these goals, the present invention provides C-20 hydroxyl of CPT to form new CPT analogs with desirable biological properties. Preferably, the present invention relates to halo-alkyl esters, of the general structure given below.

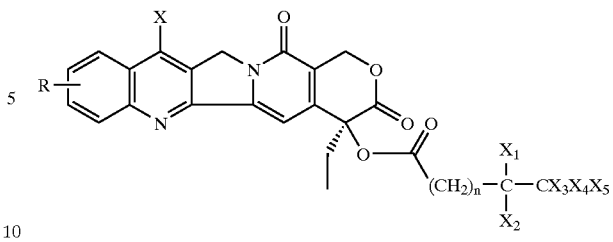

In this formula, the R group represents substituents on one of the rings of the structure above. In particular, R can represent H, $NO_2$, $NH_2$, $N_3$, —OH, a halogen (e.g., F, Cl, Br, I), carboxyl (COOH), a C1-6 alkyl group, $C_{2-16}$ alkenyl group, a $C_{3-8}$ cycloalkyl group, a $C_{1-8}$ alkoxyl group, an aroxyl group, CN, $SO_3H$, a $C_{1-8}$ halogenated alkyl group, $(CH_2)_nNR_2^7$ (where $R^7$ can be H, or a $C_{1-8}$ alkyl group, n is an integer of from 1 to about 8), hydroxyl, SH, $SR^8$ (where $R^8$ can be a $C_{1-8}$ alkyl group, or a phenyl group, or a substituted phenyl group), a carbonyl group, (e.g., $COR^9$, where $R^9$ can be a $C_{1-8}$ alkyl group, or a phenyl group, or a substituted phenyl group), a $SiR_3^{10}$ (where $R^{10}$ can be a $C_{1-4}$ alkyl group). The R group can be respectively positioned at the 9, or 10, or 11, or 12 position of ring A. R can also be a disubstituted 10, 11-O—$(CH_2)_y$—O— group (where y can be an integer of from 1 to 3). R can also be $C_{2-12}$ alkenyl group(s), $CF_3(s)$, $CCl_3(s)$, $CH_2F(s)$, $CH_2Cl(s)$, $CHF_2(s)$, $CHCl_2(s)$, OH(s), $OR^{12}(s)$ (where $R^{12}$ can be a $C_{1-8}$ alkyl group, or a $C_{2-8}$ alkenyl group, or an aromatic group), $NR_2^{13}(s)$ (where $R^{13}$ can be H, or $C_{1-4}$ alkyl group). X represents H, a $C_{1-8}$ alkyl group, a $C_{2-8}$ alkenyl group, a $C_{1-8}$ alkoxyl group, an aroxyl group, a $SiR_3^{11}$ group (where $R^{11}$ can be a $C_{1-4}$ alkyl group), or $CH_2NZY$ where Z and Y are, independently, H, $C_{1-4}$ alkyl, or a $C_{1-4}$ halogenated alkyl group. Preferably R can be H, halogen, halogen containing group, alkyl group (e.g. $C_1$–$C_{15}$ is alkyl group), $NH_2$, OH, alkoxy, or $NO_2$ n=0–18; $X_1$, $X_2$, $X_3$, $X_4$, and $X_5$, which can be the same or different, is H, a substituted or unsubstituted alkyl group, an aromatic group, or a halogen atom. At least one of $X_1$, $X_2$, and $X_5$ can be or also include a nitro group, cyano group, amino group, hydroxyl group, carbonyl group, or carboxyl group. For purposes of the present invention, preferably at least one of the $X_1$–$X_5$, is a halogen or a halogen containing group, (e.g., a halo-alkyl group or a halo-aromatic group). A preferred halogen is Cl or F. Preferably, all of $X_1$ to $X_5$ are halogen, which can be the same or different.

The various substituents described herein can be linear, branched, cyclic, or combinations thereof. Examples of alkyl groups include $C_2$–$C_{15}$ alkyl groups. Examples of alkenyl groups include $C_2$–$C_{15}$ alkenyl groups. Examples of an epoxy group includes $C_2$–$C_{15}$ epoxidized alkenyl groups. Examples of cyclo alkyl groups include $C_3$–$C_8$ cycloalkyl groups.

Some specific examples of alkyl groups that can be used are —$CH_3$, —$CH_2CH_3$, $CH_3CH_2CH_2$—, $CH_3(CH_2)_3$—, $CH_3(CH_2)_4$—, $CH_3(CH_2)_5$—, and $CH_3(CH_2)_{6-17}$—, $(CH_3)_2$CH—, $CH_3$—$CH_3$—$CH_2CH$—$CH_3$, $(CH_3CH_2)_2CH$—, $(CH_3CH_2CH_2)_2CH$—, $(CH_3)_3C$—, $CH_3(CH_3CH_2)_2C$—.

Some specific examples of alkenyl groups that can be used are $CH_2$=CH—$CH_3CH$=CH—, $CH_3CH$=C$(CH_3)$—, $CH_3CH$=CHCH$_2$—, $CH_3CH_2CH$=CHCH$_2$—, $CH_3(CH_2)_{3-15}CH$=CH—, $CH_3CH$=CH—$(CH_2)_{3-15}CH_2$, $CH_2$=CH—CH=CH—, $CH_3CH$=CH—CH=CH—, $CH_3(CH_2)_{3-6}$—CH=CH—CH=CH—$(CH_2)_{3-6}$—$CH_2$—.

Some specific examples of cycloalkoxyl groups that can be used are

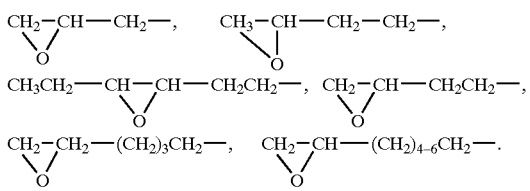

Some specific examples of alkoxyl groups that can be used are MeO—, EtO—, n-$C_3H_7$—, i-$C_3H_7$—O—, n-$C_4H_9$—O—, i-$C_4H_9$—O—, t-$C_4H_4$—O—, n-$C_5H_{11}$O—, $(CH_3)_2CHCH_2CH_2O$—,

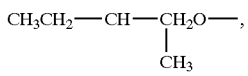

$(CH_3C_2)_2CH$—O—, n-$CH_6H_{13}$—O—, n-$C_7H_{15}$—O—, n-$C_8H_{17}$—O—.

Some specific examples of aroxyl groups that can be used are p-$CH_3OC_6H_4$—, m-$CH_3O$—$C_6H_4$—, o-$CH_3OC_6H_4$—, o,p-Dimethoxyl phenyl-, m,m-Dimethoxyl phenyl-, m,p-Dimethoxyl phenyl-, o-$CH_3CH_2OC_6H_4$—, m-$CH_3CH_2OC_6H_4$—, p-$CH_3CH_2O$—$C_6H_4$—.

Some specific examples of cycloalkyl groups that can be used are cyclo-$C_3$, cyclo-$C_4$, cyclo-$C_5$, cyclo-$C_6$, cyclo-$C_7$, cyclo-$C_8$, alkyl substituted cyclo-$C_3$, alkyl substituted cyclo-$C_4$, alkyl substituted cyclo-$C_5$, alkyl substituted cyclo-$C_6$, alkyl substituted cyclo-$C_7$, and alkyl substituted cyclo-$C_8$ (where alkyl includes preferably those alkyl groups described above).

Some specific examples of substituted and unsubstituted phenyl groups that can be used are $C_6H_5$—, (o,m,p) $CH_3C_6H_4$—, halogen substituted phenyl groups ($XC_6H_4$, wherein X=F, Cl, Br, I), (o,p,m) $CH_3OC_6H_4$—, (o,m,p) $NO_2C_6H_4$—, (o,m,p) $NH_2C_6H_4$—, (o,m,p) $CNC_6H_4$—.

Some specific examples of carbonyl groups that can be used are

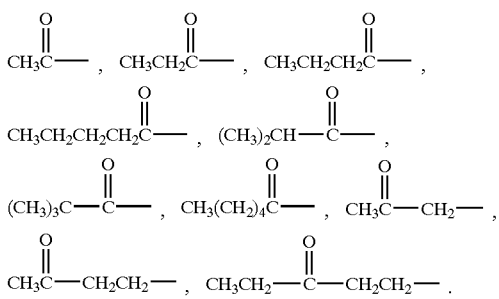

The compounds of the present invention may be produced by a variety of synthetic pathways, as would be clear to persons skilled in synthetic organic chemistry and in view of the present application. Two representative methods of producing these compounds are set forth and discussed directly below.

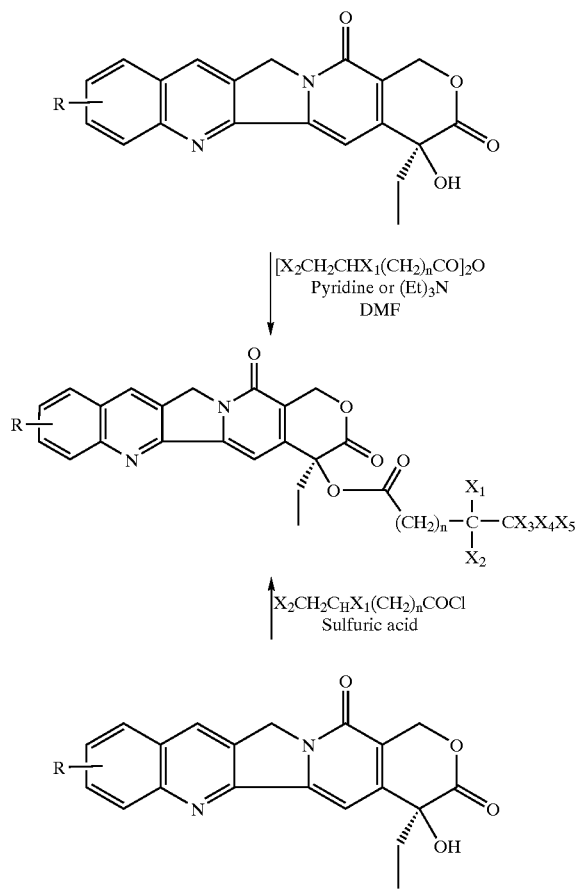

One method of making the desired product involves reacting the CPT with at least one solvent, at least one acylating agent and at least one base. The order of adding the appropriate ingredients is unimportant, but it is preferred to first mix the solvent, the CPT and the acylating agent together and then add the base to react with the product.

The purity and the concentration of the CPT is unimportant. Any solvent can be used so long as it does not include a hydroxy group, which can react with anhydrides. Thus, any solvent can be used that is capable of dissolving the CPT, but does not react with an organic anhydride.

An example of a suitable solvent is chloroform, and more preferably, dimethyl formamide (DMF).

The solvents used in this reaction are commercially available and do not need to be pure (e.g. it can be industrial-grade solvent); however, for organic reactions, it is preferable to use highly purified solvents. Additionally, the solvents can have any pH that does not cause the CPT to decompose. Preferably, the solvents are not basic, and more preferably, the solvents are neutral.

The acylating agent in the present invention can be any acylating agent that provides the acyl group of the present invention. Preferably, the acylating group is an organic anhydride. Generally, the organic anhydride can have a general formula $[X_3X_4X_5CCX_1X_2(CH_2)_nCO]_2O$ wherein n=0–18; $X_1$, $X_2$, $X_3$, $X_4$, and $X_5$, which can be the same or different, is H, a substituted or unsubstituted alkyl group, an aromatic group, or a halogen atom. At least one of $X_1$–$X_5$ can be or also include a nitro group, cyano group, amino group, hydroxyl group, carbonyl group, or carboxyl group. For purposes of the present invention, preferably at least one of the $X_1$–$X_5$, is a halogen or a halogen containing group, (e.g., a halo-alkyl group or a halo-aromatic group). A preferred halogen is Cl or F. Preferably, all of $X_1$ to $X_5$ are halogen, which can be the same or different. The organic anhydrides of the present invention are commercially available from places such as Aldrich Chemical Co., Milwaukee, Wis. One example of an organic anhydride that can be used is chloracetic anhydride, which is commercially available. The pH of the acylating agent is unimportant; however, generally acylating agents such as organic anhydrides are acidic.

The base can be any base that is capable of reacting with the product from the CPT and the acylating agent, such as an organic anhydride. However, it is preferable that the base be inert towards the CPT. Some examples of bases that are inert towards CPT are pyridine and triethylamine.

In one example of making the desired product, the CPT can be added to a solvent, which preferably is DMF. The ratio of the solvent to the CPT can be from about 10 ml or less of solvent to about 1 gram of CPT to about 1000 ml of the solvent to about 1 gram of the CPT. However, at the ratio of 1000 ml of the solvent to 1 gram of CPT more reaction time may be required. Preferably, the CPT can be added to the solvent at room temperature and atmospheric pressure in an inert atmosphere, such as $N_2$.

The acylating agent, which can be an organic anhydride having a formula $[X_5X_4X_3CX_1X_2(CH_2)_nCO]_2O$, such as chloroacetic anhydride, is commercially available and can be added to the solvent at any time. For example, it can be added to the solvent prior to adding the CPT to the solvent, while adding the CPT to the solvent, or after adding the CPT to the solvent. The ratio of the acylating agent, such as an organic anhydride to the CPT and/or solvent is unimportant so long as there is sufficient acylating agent to convert all of the mixture of the CPT and the solvent to a first product. Thus, it is preferred to have the acylating agent in excess. Although it is not necessary to agitate the mixture of the solvent, the CPT and the acylating agent, it is preferred to agitate the mixture for a short amount of time. Preferably, the mixture can be agitated by stirring the mixture at a moderate speed, such as 100 rpm.

Once the CPT, the solvent and the acylating agent are mixed together, the base is preferably added to the solution. The ratio of base to solvent preferably ranges from about 1:50 to about 1:20 percent volume. It is preferable to agitate the solution in an inert atmosphere, such as $N_2$, at a sufficient agitation speed to form the desired product. Preferably, a moderate agitation speed such as 100 rpm is used. It is common for the temperature of the reaction to increase during the reaction and reach a temperature, for instance, as high as about 100° C.

After completion of the reaction, which can be determined for instance by a change in the color of the solution, the solvent can be removed by any commonly known separation methods, such as an evaporation method or a vacuum method. The residue that remains after removing the solvent can be filtered, preferably by a column chromatography. The residue can be separated chromatographically on silica using THF-methylene chloride, preferably in a ratio of 1:15, as the eluting solvent mixture. The ratio of eluting solvent mixture can be changed depending on the compound. The final product is obtained in crystalline form upon evaporation of the proper fraction.

In the alternative, one may produce the compounds of the present invention by reacting the parent CPT with an acyl halide, preferably substituted acyl halide, in the presence of a small amount of an appropriate acid. In this method, the acyl halide replaces the organic anhydride of the previously mentioned method.

The acid used in this method can be any acid; however, the preferred acid is sulfuric acid. The pH, the concentration, and the purity of the acid is not important, so long as the impurities in the acid do not react with the CPT or the acyl halide.

Generally, the acyl halide can have a general formula $X_3X_4X_5CCX_1X_2(CH_2)_nCOZ$ wherein Z is a halogen group, such as Cl, n=0–18; $X_1$, $X_2$, $X_3$, $X_4$, and $X_5$, which can be the same or different, is H, a substituted or unsubstituted alkyl group, an aromatic group, or a halogen atom. At least one of $X_1$–$X_5$ can be or also include a nitro group, cyano group, amino group, hydroxyl group, carbonyl group, or carboxyl group. For purposes of the present invention, preferably at least one of the $X_1$–$X_5$, is a halogen or a halogen containing group, (e.g., a halo-alkyl group or a halo-aromatic group). A preferred halogen is Cl or F. Preferably, all of $X_1$ to $X_5$ are halogen, which can be the same or different. The acyl halides of the present invention are commercially available from places such as Aldrich Chemical Co., Milwaukee, Wis. Two examples of an acyl halide that can be used are chloropropionic acid and 2-chlorobutyryl chloride which are commercially available.

In this method, the CPT and acyl halide are mixed together. The ratio of the CPT to the acyl halide is not important, so long as all of the CPT is dissolved in the acyl halide. Preferably, the amount of the acyl halide to CPT is in excess to ensure that all of the CPT is dissolved.

Once the CPT and the acyl halide are added together, the mixture can be stirred for a sufficient time and a sufficient agitation speed (preferably moderate agitation, which is about 100 rpm) for the CPT and acyl halide to evenly mix.

An acid, preferably sulfuric acid, can be added to this mixture. Preferably, the acid is added to the mixture of the CPT and the acyl halide while the mixture is being stirred. Preferably, the amount of acid that can be added to the mixture is sufficient for the acid to act as a catalyst. Preferably, about 4 to about 8 glass pipet drops of the acid can be added to about 70–100 ml of the acyl halide. However, if necessary, more or less acid can be added to the mixture of the CPT and the acyl halide, preferably while the mixture is being stirred.

The mixture of CPT, acyl halide and acid can be placed in a reactor, which preferably includes an inert atmosphere, such as $N_2$, and can be heated from about 80° C. to about 120° C. Preferably, the mixture is heated from about 90° C. to about 110° C. and more preferably, the reactor is heated to about 100° C.

Preferably, the reaction will run until the desired product is formed. The reaction time can be as short as several hours to as long as several days. Preferably, the reaction time is about 15 hours under an inert atmosphere, such as $N_2$.

After completion of the reaction, which can be determined by a change in the color of the solution, the solution can be cooled to room temperature. The solvent can be removed by any commonly known separation methods, such as an evaporation method or a vacuum method. The residue that remains after removing the solvent can be separated chromatographically on silica using THF-methylene chloride, preferably in the ratio of 1:15 as the eluting solvent mixture. The final product is obtained in crystalline form upon evaporation of the proper fraction.

As set forth above, the yields of the final products in the synthetic pathways typically range from 10–90% depending on the exact reaction conditions, the purity of the starting materials, the nature of the acylating agent, the type of acid or base, and other factors or parameters common in synthetic organic chemistry. The methods of producing the compounds of the present invention, as set forth above, are not meant to be exclusive or limiting, but rather are exemplary only, and other means for generating these compounds, or optimizing the reaction conditions are possible for persons skilled in the art.

The compounds of the present invention are effective in treating malignant tumors or cancers in mammals. As used herein, the term "malignant tumor" is intended to encompass all forms of human carcinomas, sarcomas and melanomas which occur in the poorly differentiated, moderately differentiated, and well-differentiated forms.

More specifically, the compounds of the present invention and formulations of the present invention can be used in the treatment of a number of tumors and/or cancers including, but not limited to, human cancers of the lung, breast, colon, prostate, melanoma, pancreas, stomach, liver, brain, kidney, uterus, cervix, ovaries, urinary track, gastrointestinal, and other solid tumors which grow in an anatomical site other than the blood stream, as well as blood borne tumors such as leukemia. Other solid tumors include, but are not limited to, colon and rectal cancer. The compounds of the present invention are also useful as inhibitors of the enzyme topoisomerase I.

The compounds of the present invention can be administered by any acceptable route including, but not limited to, orally, intramuscularly, transdermally, intravenously, through an inhaler or other air borne delivery systems, and the like. Preferably, the compounds and the formulations of the present invention are administered orally, intramuscularly, or transdermally and most preferably delivered orally. Examples of transdermally delivery systems can be found, for instance in U.S. Pat. Nos. 5,552,154 and 5,652,244 incorporated in their entirety by reference herein. The compounds or formulations of the present invention can also be administered to a patient through a liposome system such as ones described in U.S. Pat. Nos. 5,882,679; 5,834,012; 5,783,211; 5,718,914; 5,631,237; 5,552,156; 5,059,421; 5,000,958; 5,874,105; 5,567,434; 5,549,910; 5,043,165; 5,736,156; 5,567,433; and 4,663,161, all incorporated in their entirety by reference herein. Other commonly used methods include, for example, gelatin capsules for oral administration, as well as formulations such as microsuspensions of the liposomal prodrugs in lipid and in lipid-like emulsions (e.g.-Intralipid 20, cottonseed oil and peanut oil) for intramuscular administration and inclusion in cholesterol pellets for subcutaneous long-term administration.

The compounds of the present invention may be incorporated or encapsulated in, surrounded or entrapped by, or otherwise restrained by a liposomal delivery system to form "liposomal prodrugs" using the compounds of the present invention. When taken orally by patients, the prodrugs are rapidly introduced into the bloodstream of a patient and readily converted to the parent compound in the body. Conversion of the prodrugs to the mother compound, CPT, is mediated by a group of enzymes called esterases present in the blood of many animals, including humans. Since the prodrugs are rapidly distributed throughout the body in a short period of time after delivery, these compounds exist at a very low concentration at the time they undergo enzymatic hydrolysis to the parent compound, and this prevents the CPT from precipitating in the bloodstream.

Another method of administering the compositions of the present invention is by a transdermal or transcutaneous route. One example of such an embodiment is the use of a patch. In particular, a patch can be prepared with a fine suspension of a prodrug of the present application in, for example, dimethylsulfoxide (DMSO), or a mixture of DMSO with cottonseed oil and brought into contact with the skin of the tumor carrying mammals away from the tumor location site inside a skin pouch. Other mediums or mixtures thereof with other solvents and solid supports would work equally as well for delivering the prodrugs. The patch can contain the CPT-derivative-containing prodrug of the present invention in the form of a solution or a suspension. The patch can then be applied to the skin of the patient, for example, by means of inserting it into a skin pouch of the patient formed by folding and holding the skin together by means of stitches, clips or other holding devices. This pouch should be employed in such a manner so that continuous contact with the skin is assured without the interference of the mammal. Besides using a skin pouch, any device can be used which ensures the firm placement of the patch in contact with the skin. For instance, an adhesive bandage could be used to hold the patch in place on the skin.

In addition, the compounds and formulations of the present invention can be used in combination with other drugs and formulations for the treatment of cancers such as taxol, taxotere, or their derivatives, as well as cisplatin and derivatives thereof.

As used herein, an "effective amount" of the compounds and formulations of the present invention is intended to mean that amount of the compound which will inhibit the growth of, or retard cancer, or kill malignant cells, and cause the regression and palliation of malignant tumors, i.e., reduce the volume or size of such tumors or eliminate the tumor entirely.

With mammals, including humans, the effective amounts can be administered on the basis of body surface area. The interrelationship of dosages varies for animals of various sizes and species, and for humans (based on mg/M$^2$ of body surface) is described by E. J. Freireich et al., *Cancer Chemother. Rep.*, 50(4):219 (1966). Body surface area may be approximately determined from the height and weight of an individual (see, e.g., *Scientific Tables*, Geigy Pharmaceuticals, Ardsley, N.Y. pp. 537–538 (1970). A preferred effective amount of the camptothecin compounds in the present invention can range from about 12.5 to about 31.3 mg/m$^2$ of body surface per day, and for the prodrugs an effective amount can range from about 12.5 to about 3000 mg/m$^2$ of body surface area per day based on the weight of the prodrug and the delivery system.

The preferred effective amounts or dosages of the prodrugs of the present invention in mice are from about 1 to about 400 mg prodrug per kg of body weight twice a week for an intramuscular route and about 0.75 to about 150 mg prodrug/kg/day for the oral route. Effective amounts or dosages of the prodrugs of the present invention in mice are, for instance, about 1.5 mg/kg/week to about 1000 mg/kg/week of the prodrug for the transdermal route. For all of the administering routes, the exact timing of administration of the dosages can be varied to achieve optimal results. Generally, when using Intralipid 20 as the liposomal carrier for the CPT-derivative, the actual dosage of CPT-derivative reaching the patient will be less. This is due to some loss of the CPT-derivative on the walls of the syringes, needles and preparation vessels, which is prevalent with the Intralipid 20 suspension. Generally, about 1 mg to about 4 mg of CPT-derivative is added to about 0.1 ml to about 1 ml of lipid carrier.

The compounds of the present invention may first be combined with pharmaceutically acceptable carriers or diluents, such as Intralipid 10 or 20 or natural oils, or other suitable emulsifiers for lipophilic compounds, prior to being incorporated, encapsulated, surrounded, entrapped, or otherwise restrained in, on, or by the lipsomal delivery system.

Liposomes have been used successfully to administer medications to cancer patients, and have been shown to be useful clinically in the delivery of anticancer drugs such as doxorubicin, daunorubicin, and cisplatinum complexes. Forssen, et al., Cancer Res. 1992, 52: 3255–3261; Perez-Soler, et al. Cancer Res. 1990, 50: 4260–4266; and, Khokhar, et al. J. Med. Chem. 1991, 34: 325–329, all of which are incorporated herein in their entireties by reference.

Administration involving liposomes may include, for example, lipids such as cholesterol, phospholipids, or micelles comprised of surfactant such as, for example, sodium dodecylsulfate, octylphenolpolyoxyethylene glycol, or sorbitan mono-oleate. Typically, the prodrugs bind to the lipid bilayer membrane of the liposome with high affinity. The liposome bound prodrug can preferably intercalate between the acyl chains of the lipid. The lactone ring of the camptothecin-derivative, membrane-bound prodrug is thereby removed from the aqueous environment inside and outside of the liposome and thus protected from hydrolysis. Since the liposome-bound drug is protected from hydrolysis, the antitumor activity of the drug is preserved. For the camptothecin prodrugs which have a lower affinity for the liposome membrane and thus disassociate from the liposome membrane to reside in the interior of liposome, the pH of the interior of the liposomes may be reduced thereby preventing hydrolysis of such camptothecin-derivative prodrugs.

Similarly, micelles have also been used to deliver medications to patients, (Brodin et al., Acta Pharm. Suec. 19 267–284 (1982)) and micelles have been used as drug carriers and for targeted drug delivery, (D. D. Lasic, Nature 335: 279–280 (1992); and, Supersaxo et al., Pharm. Res. 8: 1286–1291 (1991)), including cancer medications, (Fung et al., Biomater. Artif. Cells. Artif. Organs 16:439 et. seq. (1988); and Yokoyama et al., Cancer Res. 51:3229–3236 (1991)), all of which are incorporated herein in their entireties by reference.

The liposomes and/or micelles containing the camptothecin-derivative prodrugs can be administered to a cancer patient. The liposomes and/or micelles are carried by the circulatory system to the cancer cells where the membrane of the vesicle fuses to the membrane of the cancer cell thereby releasing the camptothecin-derivative prodrug to the cancer cell, or where the liposomes and/or micelles remain adjacent to the cancer cells, the camptothecin-derivative prodrug diffuses from the liposomes and/or micelles to be taken up by the cancer cells.

Any lipid or mixture of lipids which forms liposomes and/or micelles is suitable for use in the present invention. The liposomes and/or micelles may be coated with polyethyleneglycol or $GM_1$ protein which assists the particles in avoiding the reticuloendothelial system. In addition, micelles may be composed of lipid, such as phospholipid, and mixtures of lipids. Also, micelles may be composed of both lipid and a suitable surfactant.

The preparations of many liposomes and micelles are described in U.S. Pat. Nos. 5,552,156, and 5,736,156, which are herein incorporated in their entireties by reference. A preferred group of liposomal delivery systems which may be used in accordance with the present invention include those described in U.S. Pat. Nos. 5,552,156 and 5,736,156, which are herein incorporated in their entireties by reference. Other liposomal delivery systems which may be employed in accordance with the present invention include liposomes containing active agents aggregated with lipids or surfactants as described in U.S. Pat. Nos. 5,827,533 and 5,882,679; lipid vesicles formed with alkyl ammonium fatty acid salts as described in U.S. Pat. No. 5,874,105; liposomes for encapsulating active agent dry powder compositions as described in U.S. Pat. No. 5,783,211; liposomal drug delivery systems for topical patches as described in U.S. Pat. No. 5,718,914; the liposomes described in U.S. Pat. No. 5,631,237; the liposome and lipid complex compositions described in U.S. Pat. Nos. 5,549,910 and 5,077,057; the liposomes used for sustained release of steriodial drugs as described in U.S. Pat. No. 5,043,165; the liposomes described in U.S. Pat. No. 5,013,556; and the liposomes described in U.S. Pat. No. 4,663,161; all of which are herein incorporated in their entireties by reference.

The present invention also inhibits Topoisomerase I in mammals by administering an effective amount of one of the above-identified compounds using, for instance, the amounts described above. Finally, one of the most important advantages provided by the present invention relates to the relatively low or no apparent overall toxicity of the compounds administered in accordance with the teachings herein. Overall toxicity can be judged using various criteria. For example, loss of body weight in a subject over 10% of the initially recorded body weight (i.e., before treatment) can be considered as one sign of toxicity. In addition, loss of overall mobility and activity and signs of diarrhea or cystitis in a subject can also be interpreted as evidence of toxicity. In this respect, the low toxicity of the compounds and formulations of the present invention represent a significant advance over the prior art.

The present invention will be further clarified by the following examples, which are intended to be purely exemplary of the present invention.

EXAMPLES

All glassware referenced in the examples was baked at 80–100° C. for a minimum of 2 hours before being used. Melting points were obtained with a MEL-TEMP melting point apparatus and were uncorrected. The $^1H$ and $^{13}C$ NMR spectra were obtained at 270.05 MHZ with a JEOL GX-270 WB NMR spectrometer. Chemical shifts are reported in parts per million (δ scale), employing tetramethylsilane as an internal standard. In reporting the NMR data, the following abbreviations are used: coupling constants in Hertz (J), singlet (s), doublet (d), triplet (t), broad singlet (brs), multiplet (m), etc. Mass Spectra were recorded using a VG ZAB-SEQ mass spectrometer (VG Analytical Co., England) with a resolution of 10000. The numbering system used for the carbon backbone of camptothecin is shown in formula (X).

The numbering for a representative side chain is shown as below, and other derivatives having longer or shorter carbon chains are numbered according to this scheme, with the carbon having the lowest number being attached to the carbonyl carbon:

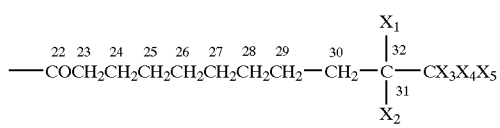

Example 1

Preparation of 9-nitrocamptothecin-20-chloroacetate (CZ236): Chloroacetic anhydride (5 g, 0.0292 mol), 9-nitrocamptothecin (4 g, ~75% pure), and 2 ml of triethylamine (Aldrich Chemical Co., Milwaukee, Wis.) were added to 100 ml DMF in a three-necked round-bottom flask equipped with a mechanic stirrer. The mixture was stirred under room temperature for 72 hr. The residue was then chromatographically separated with THF-Methylene chloride (ratio: 1:15) as eluent. The solvent was removed with a rotary evaporator. The pure product was obtained as a brown powder, yield 25%.

Example 2

Preparation of camptothecin 20-O-(3'-chloro)propionate (CZ280): Camptothecin (5 g, 0.01471 mol, commercially available in China and other locations and purified in the laboratory), and chloropropionic acid chloride (75 ml, Aldrich Chemical Co.) were added to a 200 ml round-bottomed flask equipped with a magnetic stirrer. To the mixture, was added 4 to 6 drops of concentrate sulfuric acid. The mixture was stirred at 100±10° C. for 15 hr. After cooling to room temperature, the solvent was removed with a rotary evaporator. The residue was chromatographically separated with THF-methylene chloride solvent system as eluent. The pure product was obtained as yellowish crystals, yield 47%, mp 255° C. $^1$H NMR(CHCl$_3$): 0.860(5H, t, J=7.250 Hz, C19-methylprotons), 2.091–2.338(2H, m, C18-methylene protons), 3.000(2H, t, J=7.285 Hz, C23-methylene protons), 3.775(2H, t, J=7.261 Hz, C24-methylene protons), 5.280 (2H, s, C5-methylene protons), 5.350–5.720(2H, dd, J=17.120, 17.125 Hz, C17-methylene protons), 7.240(1H, s, C14-H), 7.658(1H, t, J=9.025 Hz, C10-H), 7.810(1H, t, J=9.102 Hz, C11-H), 7.90(1H, d, J=9.380 Hz, C9-H), 8.200 (1H, d, J=9.368 Hz, C12-H), 8.385(1H, s, C7-H). —C:7.568 (C19), 32.000(C18), 37.800, 38.535(C23, C24), 50.125(C5), 67.155(C17), 96.88(C14), 120.250, 127.120, 178.250, 178, 500, 129.625, 130.750, 131.252, 132.912, 145.510, 146.452, 149.001, 152.500, 157.512(C2, C3, C6–C16a), 167.100, 169.450(C21, C22), C20 buried in the area of solvent peaks.

Example 3

Preparation of camptothecin 20-O-(4'-chloro)butyrate (CZ281): With the same procedure as preparation of CZ280 and using 4-chlorobutyryl chloride as acylating agent, the pure CZ281 was obtained as white crystals, yield 82%, mp 265° C. $^1$H NMR (CDCl$_3$): 0.989(3H, t, J=7.210 Hz, C19-methyl protons), 2.051–2.35(4H, m, C18- and C24-methylene protons), 2.600–2.800(2H, m, C23-methylene protons), 3.605(2H, t, J=7.223 Hz, C24-methylene protons), 5.301(2H, s, C5-methylene protons), 5.350–5.760(2H, dd, J=17.098, 17.123 Hz, C17-methylene protons), 7.220(1H, s, C14-H), 7.668(1H, t, J=8.980 Hz, C10-H), 7.835(1H, t, J=8.899 Hz, C11-H), 7.975(1H, d, J=9.012 Hz, C9-H), 8.250(1H, d, J=9.075 Hz, C12-H), 8.400(1H, s, C7-H). $^{13}$C: 7.520(C19), 27.610, 30.750, 32.000, 43.850(C18, C23, C24, and C25), 50,000(C5), 67.010(C17), 76.125(C20), 95.988 (C14), 120.180, 128.440, 128.5.5, 129.891, 130.750, 131.180, 145.650, 146.200, 148.760, 152.256, 187.212(C2, C3, C6–C16a), 167.488, 171.650(C21, C22).

Example 4

Preparation of 9-nitrocamptothecin 20-O-3'-chloropropionate (CZ285): Using 9-nitrocamptothecin as starting material and with the same procedure as described in Example 2, the pure CZ285 was obtained as a yellow powder, yield 71%, mp 200° C. $^1$H NMR(CDCl$_3$): 1.053 (3H, t, J=7.210 Hz, C19-methyl protons), 2.120–2.310(2H, m, C18-methylene protons), 3.051(2H, t, J=7.015 Hz, C23-methylene protons), 3.750(2H, t, J=7.123 Hz, C24-methylene protons), 5.468(2H, s, C5-methylene protons), 5.470–5.765(2H, dd, J=17.250, 17.286 Hz, C17-methylene protons), 7.305(1H, s, C14-H), 7.930(1H, t, J=9.012 Hz, C11-H), 8.485–8.550(2H, m, C9-H and C12-H), 9.280(1H, s, C7-11). $^{13}$C NMR:7.670(C19), 32.010(C18), 37.610 (C23), 38.899(C24), 50.501(C5), 67.315(C17), 97.120 (C14), 121.510, 125.915, 127.496, 128.668, 131.751, 136.615, 145.005, 145.610, 146.010, 149.005, 157.250(C2, C3, C6–C16a), 167.100, 169.230(C21, C22). C20 buried in the area of solvent peaks.

Example 5

Preparation of 9-nitrocamptothecin 20-O-4'-chlorobutyrate (CZ288): With the same procedure as described in Example 2, using 4-chlorobutyryl chloride as acylating agent, the pure CZ288 was obtained yellow powders, yield 50%, mp 254° C. $^1$H NMR(DMSO): 0.950 (3H, t, J=7.238 Hz, C19-methylprotons), 1.987–2.205(4H, m, C18- and C22-methylene protons), 2.758(2H, t, J=7.150 Hz, C23-methylene protons), 4.780(2H, t, J=7.213 Hz, C25-methylene protons), 5.340(2H, s, C5-methylene protons), 5.528(2H, s, C17-methylene protons), 7.150(1H, s, C14-H), 8.075(1H, t, J=8.689 Hz, C11-H), 8.480–8.550(2H, m, C10- and C12-Hs), 9.160(1H, s, C7-H). $^{13}$C NMR(DMSO): 7.600 (C19), 28.001(C24), 30.500, 30.655(C18, C23), 44.125 (C25), 51.500(C5), 67.100(C17), 76.155(C20), 95.898 (C14), 120.012, 120.500, 125.512, 126.600, 120.412, 133.000, 135.698, 145.012, 145.045, 146.010, 147.998, 153.850, 156.505(C2, C3, C6–C16a), 167.005, 171.586 (C21, C22).

Example 6

The sample of CZ281 submitted for analysis was examined microscopically and found to be visually homogeneous in composition. Several well-formed specimens were cleaved to yield crystals with dimensions of 0.1 to 0.4 mm. Three were mounted on fine glass fibers with a high-viscosity mineral oil and cooled to −100° C. All three crystals yielded the same unit cell dimensions and orthorhombic diffraction symmetry. The chiral space group P2$_1$2$_1$2$_1$ was uniquely determined from systematic absences in the diffraction data. Details of the experimental parameters are given in Table 1.

Approximately two octanes of data were collected at −100° C. using a Siemens four-circle diffractometer coupled to a highly sensitive CCD detector and MoKα radiation. From these data, 3729 symmetry independent reflections were harvested. The structure was solved by direct methods and refined with anisotropic thermal parameters for all non-hydrogen atoms. Hydrogen atoms were treated as idealized contributions. A parameter sensitive to the absolute configuration was refined; its final value confirmed that the enantiomer reported is correct to better than a 99.9% confidence level.

All software used in the data processing is contained in SHELXTL library (version 5.1, G. Sheldrick, Bruker AXS, Madison, Wis.).

Other embodiments of the present invention will be apparent to those skilled in the art from consideration of the specification and practice of the invention disclosed herein. It is intended that the specification and examples be considered as exemplary only, with a true scope and spirit of the invention being indicated by the following claims and equivalents thereof.

What is claimed is:

1. A compound of formula I:

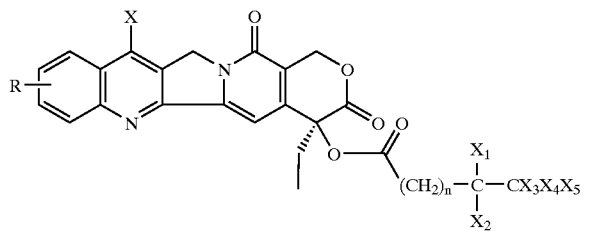

wherein R is H, —OH, $NO_2$, $NH_2$, $N_3$, a halogen, carboxyl, a $C_{1-16}$ alkyl group, a $C_{2-16}$ alkenyl group, a $C_{3-8}$ cycloalkyl group, a $C_{1-8}$ alkoxyl group, an aroxyl group, CN, $SO_3H$, a $C_{1-8}$ halogenated alkyl group, $(CH_2)_nNR_2^7$, hydroxyl, SH, $SR^8$, a carbonyl group, a $SiR_3^{10}$; $C_{2-12}$ alkenyl group, $CF_3$, $Cl_3$, $CH_2F$, $CH_2Cl$, $CHF_2$, $CHCl_2$, OH, or $OR^2$; wherein said R group is respectively positioned at 9, 10, 11, or 12 position of ring A; $R^{12}$ is a $C_{1-8}$ alkyl group, a $C_{2-8}$ alkenyl group, or an aromatic group; $R^7$ is H or a $C_{1-8}$ alkyl group; n is an integer of 1 to 8; $R^8$ is a $C_{1-8}$ alkyl group or a substituted or unsubstituted phenyl group; $R^{10}$ is a $C_{1-4}$ alkyl group; X is H, a $C_{1-8}$ alkyl group, a $C_{2-8}$ alkenyl group, a $C_{1-8}$ alkoxyl group, an aroxyl group, a $SiR_3^{11}$ group, or $CH_2NZY$; n is 1 through 18; and wherein $X_1$, $X_2$, $X_3$, $X_4$, and $X_5$, which are the same or different, is hydrogen, halogen, substituted or unsubstituted alkyl group, aromatic group, nitro group, cyano group, amino group, hydroxyl group, carbonyl group, carboxyl group, with the proviso that at least one of $X_1$ through $X_5$ is a halogen atom or a halogen containing group.

2. The compound of claim 1, wherein $X_1$, $X_3$ and $X_4$ are hydrogen, and $X_2$ and $X_5$ are halogen, which are the same or different.

3. The compound of claim 1, wherein $X_1$ and $X_2$ are hydrogen, and $X_3$, $X_4$, and $X_5$ are halogen, which are the same or different.

4. The compound of claim 1, wherein $X_1$, $X_2$ and $X_3$ are hydrogen, and $X_4$ and $X_5$ are halogen, which are the same or different.

5. compound of claim 1, wherein $X_3$, and $X_4$ are hydrogen, and $X_1$, $X_2$, and $X_5$ are halogens, which are the same or different.

6. The compound of claim 2, wherein $X_2$ and $X_5$ are fluorine or chlorine, which are the same or different.

7. The compound of claim 3, wherein $X_3$, $X_4$, and $X_5$ are fluorine or chlorine, which are the same or different.

8. The compound of claim 4, wherein $X_4$ and $X_5$ are fluorine or chlorine, which are the same or different.

9. The compound of claim 5, wherein $X_1$, $X_2$, and $X_5$ are fluorine or chlorine, which are the same or different.

10. The compound of claim 1, wherein $X_1$ is halogen, and $X_2$, $X_3$, $X_4$, and $X_5$ are hydrogen.

11. The compound of claim 1, wherein $X_3$ is halogen, and $X_1$, $X_2$, $X_4$, and $X_5$ are hydrogen.

12. The compound of claim 10, wherein $X_1$ is chlorine.

13. The compound of claim 10, wherein $X_1$ is fluorine.

14. The compound of claim 11, wherein $X_3$ is fluorine.

15. The compound of claim 11, wherein $X_3$ is chlorine.

16. A method for treating a tumor or cancer in a mammal comprising administering a composition comprising an effective amount of said compound of claim 1, wherein said tumor or cancer is responsive to said composition.

17. A method for treating a tumor or cancer in a mammal comprising administering a composition comprising an effective amount of said compound of claim 2, wherein said tumor or cancer is responsive to said composition.

18. A method for treating a tumor or cancer in a mammal comprising administering a composition comprising an effective amount of said compound of claim 3, wherein said tumor or cancer is responsive to said composition.

19. A method for treating a tumor or cancer in a mammal comprising administering a composition comprising an effective amount of said compound of claim 4, wherein said tumor or cancer is responsive to said composition.

20. A method for treating a tumor or cancer in a mammal comprising administering a composition comprising an effective amount of said compound of claim 5, wherein said tumor or cancer is responsive to said composition.

21. A method for treating a tumor or cancer in a mammal comprising administering a composition comprising an effective amount of said compound of claim 6, wherein said tumor or cancer is responsive to said composition.

22. A method for treating a tumor or cancer in a mammal comprising administering a composition comprising an effective amount of said compound of claim 7, wherein said tumor or cancer is responsive to said composition.

23. A method for treating a tumor or cancer in a mammal comprising administering a composition comprising an effective amount of said compound of claim 8, wherein said tumor or cancer is responsive to said composition.

24. A method for treating a tumor or cancer in a mammal comprising administering a composition comprising an effective amount of said compound of claim 9, wherein said tumor or cancer is responsive to said composition.

25. A method for treating a tumor or cancer in a mammal comprising administering a composition comprising an effective amount of said compound of claim 10, wherein said tumor or cancer is responsive to said composition.

26. A method for treating a tumor or cancer in a mammal comprising administering a composition comprising an effective amount of said compound of claim 11, wherein said tumor or cancer is responsive to said composition.

27. A method for treating a tumor or cancer in a mammal comprising administering a composition comprising an effective amount of said compound of claim 12, wherein said tumor or cancer is responsive to said composition.

28. A method for treating a tumor or cancer in a mammal comprising administering a composition comprising an effective amount of said compound of claim 13, wherein said tumor or cancer is responsive to said composition.

29. A method for treating a tumor or cancer in a mammal comprising administering a composition comprising an effective amount of said compound of claim 14, wherein said tumor or cancer is responsive to said composition.

30. A method for treating a tumor or cancer in a mammal comprising administering a composition comprising an effective amount of said compound of claim 15, wherein said tumor or cancer is responsive to said composition.

31. The method of claim 16, wherein said tumor or cancer is present in lung, breast, colon, prostate, pancreas, stomach, liver, brain, kidney, uterus, cervix, ovaries, urinary tract, rectal tract, or is a melanoma or leukemia.

32. The method of claim 17, wherein said tumor or cancer is present in said lung, breast, colon, prostate, pancreas, stomach, liver, brain, kidney, uterus, cervix, ovaries, urinary tract, rectal tract, or is a melanoma or leukemia.

33. The method of claim 18, wherein said tumor or cancer is present in said lung, breast, colon, prostate, pancreas, stomach, liver, brain, kidney, uterus, cervix, ovaries, urinary tract, rectal tract, or is a melanoma or leukemia.

34. The method of claim 19, wherein said tumor or cancer is present in said lung, breast, colon, prostate, pancreas, stomach, liver, brain, kidney, uterus, cervix, ovaries, urinary tract, rectal tract, or is a melanoma or leukemia.

35. The method of claim 20, wherein said tumor or cancer is present in said lung, breast, colon, prostate, pancreas, stomach, liver, brain, kidney, uterus, cervix, ovaries, urinary tract, rectal tract, or is a melanoma or leukemia.

36. The method of claim 21, wherein said tumor or cancer is present in said lung, breast, colon, prostate, pancreas, stomach, liver, brain, kidney, uterus, cervix, ovaries, urinary tract, rectal tract, or is a melanoma or leukemia.

37. The method of claim 22, wherein said tumor or cancer is present in said lung, breast, colon, prostate, pancreas, stomach, liver, brain, kidney, uterus, cervix, ovaries, urinary tract, rectal tract, or is a melanoma or leukemia.

38. The method of claim 23, wherein said tumor or cancer is present in lung, breast, colon, prostate, pancreas, stomach, liver, brain, kidney, uterus, cervix, ovaries, urinary tract, rectal tract, or is a melanoma or leukemia.

39. The method of claim 24, wherein said tumor or cancer is present in said lung, breast, colon, prostate, pancreas, stomach, liver, brain, kidney, uterus, cervix, ovaries, urinary tract, rectal tract, or is a melanoma or leukemia.

40. The method of claim 25, wherein said tumor or cancer is present in said lung, breast, colon, prostate, pancreas, stomach, liver, brain, kidney, uterus, cervix, ovaries, urinary tract, rectal tract, or is a melanoma or leukemia.

41. The method of claim 26, wherein said tumor or cancer is present in said lung, breast, colon, prostate, pancreas, stomach, liver, brain, kidney, uterus, cervix, ovaries, urinary tract, rectal tract, or is a melanoma or leukemia.

42. The method of claim 27, wherein said tumor or cancer is present in said lung, breast, colon, prostate, pancreas, stomach, liver, brain, kidney, uterus, cervix, ovaries, urinary tract, rectal tract, or is a melanoma or leukemia.

43. The method of claim 28, wherein said tumor or cancer is present in said lung, breast, colon, prostate, pancreas, stomach, liver, brain, kidney, uterus, cervix, ovaries, urinary tract, rectal tract, or is a melanoma or leukemia.

44. The method of claim 29, wherein said tumor or cancer is present in said lung, breast, colon, prostate, pancreas, stomach, liver, brain, kidney, uterus, cervix, ovaries, urinary tract, rectal tract, or is a melanoma or leukemia.

45. The method of claim 30, wherein said tumor or cancer is present in said lung, breast, colon, prostate, pancreas, stomach, liver, brain, kidney, uterus, cervix, ovaries, urinary tract, rectal tract, or is a melanoma or leukemia.

46. A method for inhibiting an enzyme responsible for hydrolyzing lactone ring of camptothecin under biological conditions, by administering a composition comprising said compound of claim 1 to a mammal.

47. A method for inhibiting an enzyme responsible for hydrolyzing lactone ring of camptothecin under biological conditions, by administering a composition comprising said compound of claim 1 to a mammal, wherein said enzyme is topoisomerase I.

48. A method of making a halo-alkyl ester of claim 1 comprising:
  mixing a camptothecin, a solvent, an acylating agent, and a base in any order.

49. The method of claim 48, wherein said solvent is a solvent capable of dissolving said camptothecin, but incapable of reacting with said acylating agent.

50. The method of claim 48, wherein said solvent does not include a hydroxy group.

51. The method of claim 48, wherein said solvent is dimethyl formamide.

52. The method of claim 48, wherein said acylating agent is mixed with said solvent before, during or after mixing said camptothecin with said solvent.

53. The method of claim 48, wherein said acylating agent is an organic anhydride.

54. A method of making a halo-alkyl ester of claim 1 comprising:
  mixing a camptothecin, an acyl halide, and an acid in any order.

55. The method of claim 54, wherein said acid is sulfuric acid.

56. The method of claim 54, further comprising heating mixture of said camptothecin, acyl halide, and acid from about 80° C. to about 120° C. in an inert atmosphere.

* * * * *

UNITED STATES PATENT AND TRADEMARK OFFICE
CERTIFICATE OF CORRECTION

PATENT NO. : 6,703,399 B2
DATED : March 9, 2004
INVENTOR(S) : Cao et al.

It is certified that error appears in the above-identified patent and that said Letters Patent is hereby corrected as shown below:

<u>Column 17,</u>
Line 19, "Cl$_3$" should read -- CCl$_3$ --.
Line 41, add -- The -- before "compound"

Signed and Sealed this

Twenty-fifth Day of May, 2004

JON W. DUDAS
*Acting Director of the United States Patent and Trademark Office*